US00PP11150P

United States Patent [19]

van Andel

[11] Patent Number: Plant 11,150

[45] Date of Patent: Dec. 7, 1999

[54] ALSTROEMERIA PLANT NAMED 'STAPRIMAR'

[75] Inventor: Jacob van Andel, Aalsmeer, Netherlands

[73] Assignee: Van Staaveren B.V., Aalsmeer, Netherlands

[21] Appl. No.: 09/021,493

[22] Filed: Feb. 10, 1998

[51] Int. Cl.[6] ..... A01H 5/00

[52] U.S. Cl. ..... Plt./309

[58] Field of Search ..... Plt./309

*Primary Examiner*—Howard J. Locker

*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria which is a cross of two unnamed, undistributed seedlings; namely, 91D211-11 as seed parent and 87G1069-2 as pollen parent. The varietal denomination of the new variety is 'Staprimar'.

The first act of asexual reproduction of 'Staprimar' was in Aalsmeer, The Netherlands, by propagation by dividing the rhizomes and tissue culture. Asexual reproduction by dividing rhizomes through successive generations in Aalsmeer, The Netherlands, has demonstrated that the combination of characteristics as herein disclosed for 'Staprimar' are firmly fixed and retained through successive generations.

SUMMARY OF THE INVENTION

The new variety of Alstroemeria, 'Staprimar', produces large long lasting leaves and pink flowers on strong stems.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid plants about one year old as observed in a greenhouse in Aalsmeer, The Netherlands in the month of October. Color designations indicated are in accordance with The Royal Horticultural Society Color Chart by color plate designations.

'Staprimar' has not been observed under all possible environmental conditions. Phenotypic expression may vary with variations in environment such as temperature, light intensity, day length and growing and cultural conditions.

Botanical classification:
- *Family.*—Amaryllidaceae.
- *Genus.*—Alstroemeria sp.
- *Commercial.*—Alstroemeria hybrid.

Origin: Seedling.

PLANT

Form: Bush useful as pot plant or garden decoration.
Shape: Upright.
Height: About 25 to 45 cm.
Branching characteristics: Flower stems do not branch.

Blooming habit: Recurrent — From April up to and including October in the Netherlands.
Disease resistance: Unknown.
Foliage:
- *Quantity.*—Abundant.
- *Number of leaves.*—About 25 to 30.
- *Size of leaf.*—Length: About 3 to 10 cm. Width: About 1 to 2 cm.
- *Shape of leaf.*—Elliptic.
- *Margin.*—Minutely crimped.
- *Texture.*—Glossy.
- *Color.*—Upper side: Near 137A. Underside: Near 137C.
- *Venation.*—Curved.
- *Rhizomes.*—Color: Near 155D. Size: About 10 to 25 cm.

FLOWER

Size (when first anthers release pollen):
- *Diameter.*—About 6 to 7 cm.
- *Depth.*—About 4 to 5 cm.

Borne: Singly along simple racemes.
Discoloration after full bloom: No.
Shape or form:
- *When bloom first opens.*—Cup.

When bloom matures: Cup.
Fragrance: None.
Lasting quality:
- *On plant.*—About 21 days.
- *As cut flower.*—About 14 days.

Tepals:
- *Number of tepals.*—About 6.
- *Arrangement.*—2 concentric circles of 3 tepals.
- *Shape.*—Tepals — obovate; bloom — cup shaped.
- *Margin.*—Slightly serrated.
- *Apex.*—Pointed.
- *Size of bloom fully expanded.*—Diameter about 6 to 7 cm, depth about 4 to 5 cm.
- *Texture.*—Soft.
- *Color.*—Outer tepals (lateral and median) near 62C, about 1 to 5 stripes near 185A; inner lateral tepals near 62C with yellow center near 13A, around the yellow center there is a white spot near 155D, inner median tepal has no yellow center but has a very light pink color near 62D; the inner lateral and median tepals have 30 to 40 stripes near 185A.

Flower stem: Length about 2 to 3 cm; diameter about 0.5 cm; peduncle about 2 to 6 cm.
- *Color.*—Near 137A.
- *Strength.*—Strong.

*Number of blooms per stem.*—About 2 to 3, very small.
*Hairy.*—No.
Persistence: Flower does not hang on and dry.

BUD

Size:
*Diameter.*—About 0.5 to 1.0 cm.
*Depth or length.*—About 1 to 2 cm.
Form: Pear-shaped.
Rate of opening: Fast.
Color of tepals:
*When tepals begin to unfurl.*—Young buds near 155D, then near 62C when bud starts to open.

REPRODUCTIVE ORGANS

Stamen:
*Number.*—About 6.
*Arrangement.*—Around the style.
Anthers:
*Size.*—About 0.5 to 1.0 cm.
*Color.*—Near 152C.
Filaments:
*Length.*—About 5 cm.
*Color.*—Near 62C.
Pollen:
*Color.*—Near 152A.
Pistils:
*Styles.*—Length about 4 to 6 cm.
*Color of styles.*—Near 62C.
Stigmas:
*Color.*—Near 62D.

FRUIT

Fertile: Yes.
Shape: Round, about 1 to 2 cm.
Color at maturity: Near 164A.

I claim:

1. A new Alstroemeria plant of the variety substantially as herein shown and described.

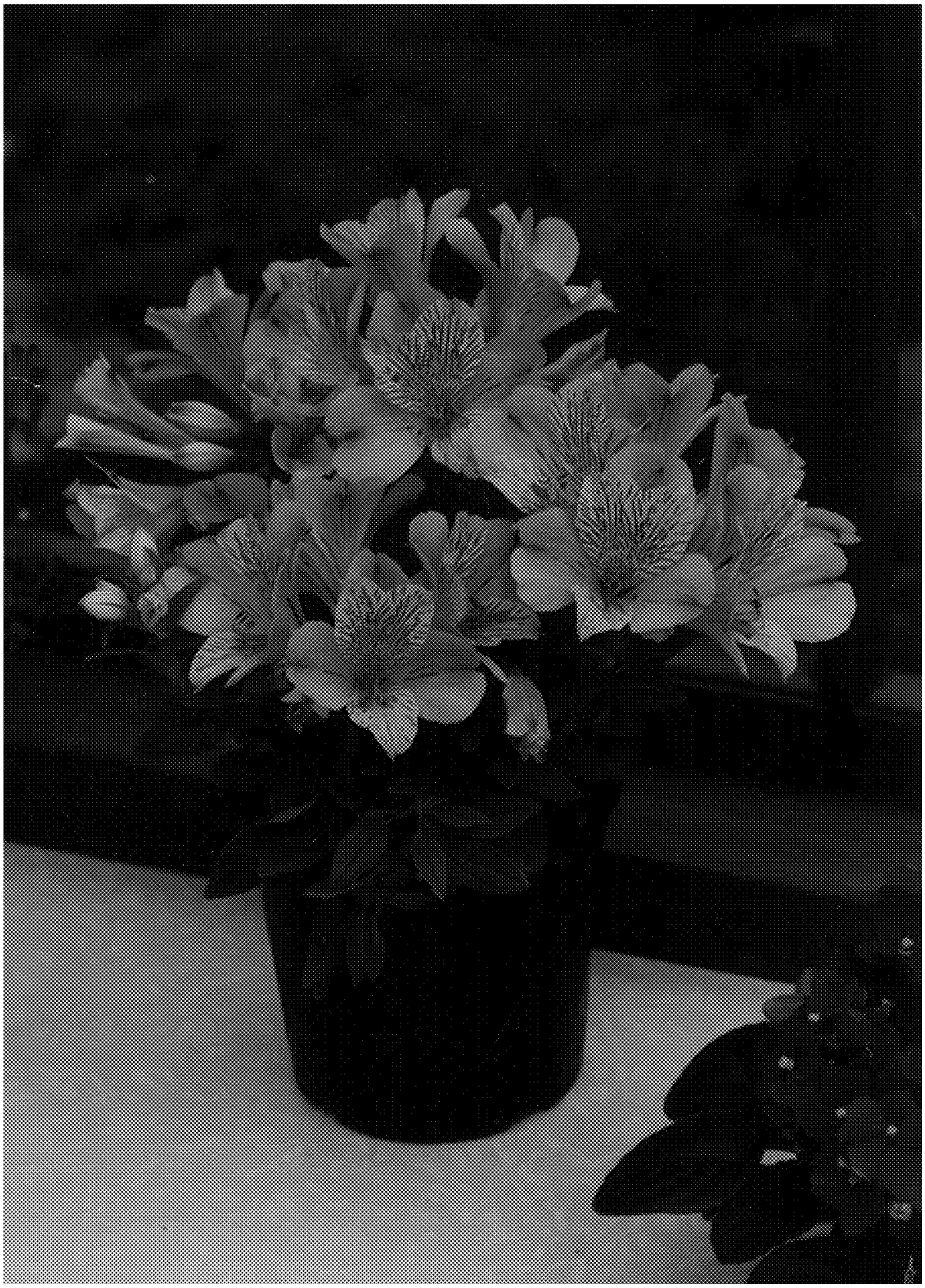

* * * * *